(12) United States Patent
Mercado

(10) Patent No.: US 11,452,635 B2
(45) Date of Patent: *Sep. 27, 2022

(54) SURGICAL SYSTEMS INCLUDING A POWER LOSS MITIGATION SUBSYSTEM

(71) Applicant: Alcon Inc., Fribourg (CH)

(72) Inventor: Fred Mercado, Laguna Hills, CA (US)

(73) Assignee: Alcon Inc., Fribourg (CH)

( * ) Notice: Subject to any disclaimer, the term of this patent is extended or adjusted under 35 U.S.C. 154(b) by 474 days.

This patent is subject to a terminal disclaimer.

(21) Appl. No.: 16/676,696

(22) Filed: Nov. 7, 2019

(65) Prior Publication Data

US 2020/0069467 A1 Mar. 5, 2020

Related U.S. Application Data

(63) Continuation of application No. 15/096,452, filed on Apr. 12, 2016, now Pat. No. 10,517,757.

(51) Int. Cl.
*A61F 9/007* (2006.01)
*H02J 9/06* (2006.01)
*A61M 1/00* (2006.01)
*A61B 17/00* (2006.01)

(52) U.S. Cl.
CPC ...... *A61F 9/00736* (2013.01); *A61F 9/00763* (2013.01); *A61M 1/0058* (2013.01); *H02J 9/061* (2013.01); *A61B 2017/00017* (2013.01); *A61B 2017/00199* (2013.01); *A61B 2017/00225* (2013.01); *A61B 2017/00734* (2013.01); *A61B 2017/00973* (2013.01); *A61B 2217/005* (2013.01); *A61B 2217/007* (2013.01); *A61B 2560/0214* (2013.01); *A61M 2205/16* (2013.01); *A61M 2210/0612* (2013.01)

(58) Field of Classification Search
CPC .. A61F 9/00736; A61F 9/00763; A61B 90/37; A61M 1/0058; H02J 9/061
USPC ........................................................ 604/264
See application file for complete search history.

(56) References Cited

U.S. PATENT DOCUMENTS

| | | | |
|---|---|---|---|
| 5,461,263 A | * | 10/1995 | Helfrich ................ H02J 9/062 307/64 |
| 6,117,126 A | * | 9/2000 | Appelbaum ........ A61F 9/00763 606/4 |
| 6,175,166 B1 | | 1/2001 | Bapat |
| 8,037,354 B2 | | 10/2011 | Majewski |
| 8,374,012 B2 | | 2/2013 | Raptis |
| 8,710,820 B2 | | 4/2014 | Parker |
| 9,250,675 B2 | | 2/2016 | Massarotti |

* cited by examiner

*Primary Examiner* — Phillip A Gray

(57) ABSTRACT

Systems, circuits, and methods to mitigate effects of short-term power losses in medical systems are provided. An exemplary surgical system includes a fluidics subsystem, a surgical instrument subsystem that couples to a surgical instrument and a power supply subsystem coupled to the surgical instrument subsystem. The power supply subsystem includes a main power supply connectable to AC mains to generate a voltage, a power bus connected to the main power supply, an alternate power supply, and a circuit that monitors the voltage on the power bus for powering the surgical instrument subsystem. The circuit automatically connects the power bus to the alternate power supply when the voltage drops below a reference voltage due to a power loss from the main power supply.

16 Claims, 5 Drawing Sheets

SURGICAL SYSTEMS INCLUDING A POWER LOSS MITIGATION SUBSYSTEM

This application is a continuation of U.S. Non-Provisional Patent Application Ser. No. 15/096,452 titled "SURGICAL SYSTEMS INCLUDING A POWER LOSS MITIGATION SUBSYSTEM," filed on Apr. 12, 2016, whose inventor is Fred Mercado, which is hereby incorporated by reference in its entirety as though fully and completely set forth herein.

TECHNICAL FIELD

The present disclosure is directed to methods and systems for maintaining a continuous power supply for a medical system or device during a power interruption.

BACKGROUND

Increasingly, medical procedures are performed in connection with the use of sophisticated medical systems, such as diagnostic systems, monitoring systems, and surgical systems. The sophisticated medical systems may rely on complex electronics and complex circuits to perform their diagnostic, monitoring, and surgical tasks. The degree of importance of maintaining a continuous power supply to such medical systems can vary according to the tasks associated with such systems.

For example, when a surgeon is performing a surgical procedure using a surgical system or instrument and the system or instrument experiences even a short-term power loss, the short-term power loss may alter the performance of the system or instrument in such a way that adversely affect the efficacy and results of the procedure. The complexity of the machine and the nature of the procedure may increase the risks associated with such short-term power losses. While efforts are taken to maintain continuous power in the power grid, there is still a need to provide for a power loss mitigation system at the level of the medical systems themselves.

SUMMARY

The present disclosure is directed to systems, circuits, and methods for mitigating temporary power losses.

Exemplary medical systems are provided herein. An exemplary ophthalmic surgical system may include a fluidics subsystem, a surgical instrument subsystem that couples to a surgical instrument, and a power supply subsystem coupled to the surgical instrument subsystem. The fluidics subsystem may be coupled to the surgical instrument subsystem. The power supply subsystem may include a main power supply connectable to AC mains to generate a voltage, a power bus connected to the main power supply, an alternate power supply, and a circuit that monitors the voltage on the power bus for powering the surgical instrument subsystem. The circuit may automatically connect the power bus to the alternate power supply when the voltage drops below a reference voltage due to a power loss from the main power supply.

Other exemplary systems are provided herein. An exemplary surgical system may include a surgical instrument subsystem and a power supply subsystem coupled to the surgical instrument subsystem. The surgical instrument subsystem may be connected to a surgical instrument. The power supply subsystem may include a main power supply connectable to AC mains to generate a voltage, a power bus connected to the main power supply, an alternate power supply, and a circuit that monitors the voltage on the power bus. The circuit may automatically connect the power bus to the alternate power supply when the voltage drops below a reference voltage due to a power loss from the main power supply.

Exemplary methods of mitigating a short-term power loss in a surgical system are provided. An exemplary method may include detecting, at a first point in time, a difference between a power supply voltage on a power bus in the surgical system and a reference voltage, connecting the power bus to an alternate power supply contained within a housing of the surgical system, and detecting, at a second point in time that is subsequent to the first point in time, that the power supply voltage is greater than the reference voltage. The exemplary method may further include disconnecting the alternate power supply from the power bus of the surgical system.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the devices and methods disclosed herein and together with the description, serve to explain the principles of the present disclosure.

Figure 1:
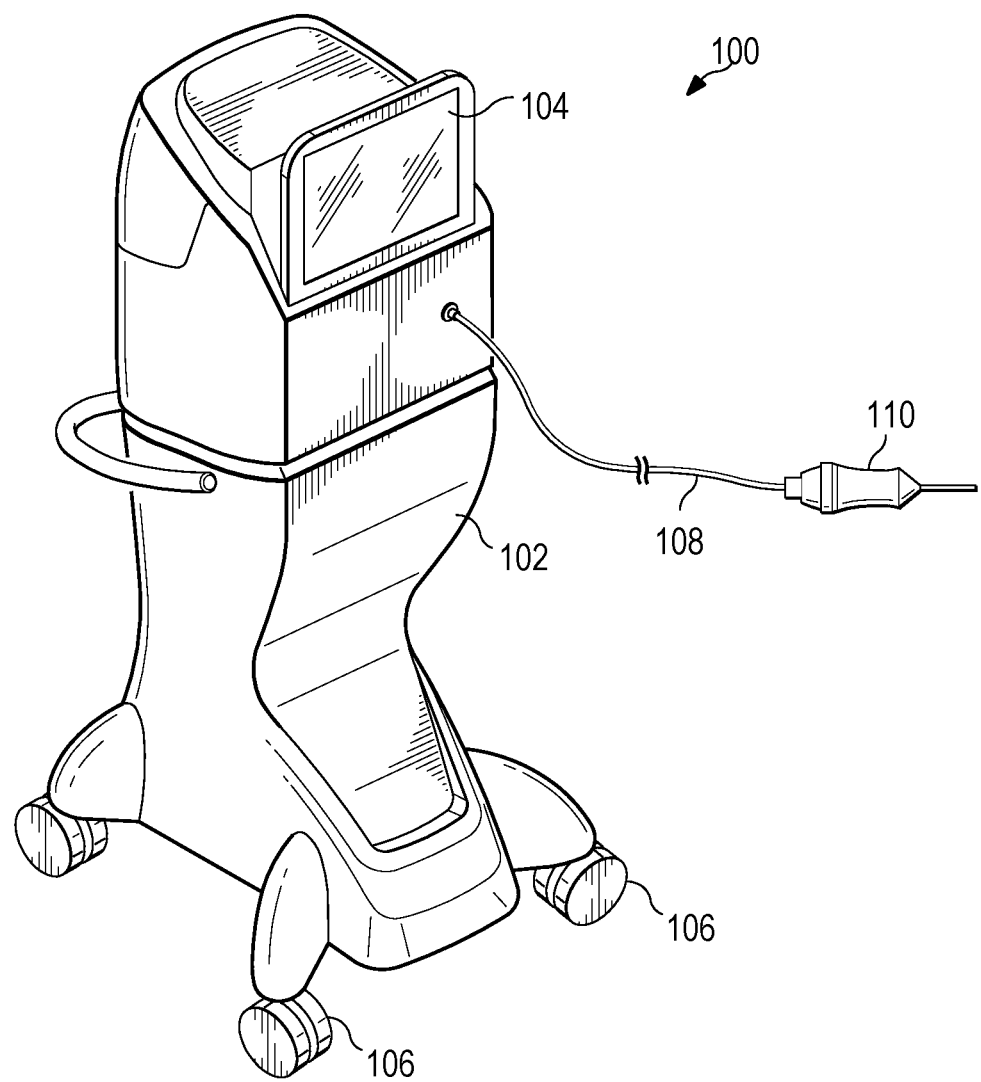
FIG. 1 illustrates a perspective view of an exemplary surgical system.

The accompanying drawings may be better understood by reference to the following detailed description.

DETAILED DESCRIPTION

For the purposes of promoting an understanding of the principles of the present disclosure, reference will now be made to the implementations illustrated in the drawings. Specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For example, although explanatory references are made to "surgical systems," other medical systems are included within the scope of the present disclosure. For simplicity, in some instances the same reference numbers are used throughout the drawings to refer to the same or like parts.

The present disclosure is directed to systems, circuits, and methods for providing a continuous power supply during short-term power losses. Such power losses include decreases in power outside of normal operating requirements, as well as complete power outages in which no electrical power is supplied. The short-term power losses may be power losses ranging from a few milliseconds to 300, 500, or 1000 milliseconds (ms) or longer, for example. During a surgical procedure, including diagnostic and interventional procedures, such power losses may adversely affect the effectiveness and overall results of the procedure. For example, if a user, such as a surgeon or other medical professional, is performing a surgery on the eye of a patient using a vitrectomy cutter, a loss in power may change the performance of the vitrectomy cutter. The user may respond to the loss in power by increasing a pressure or by otherwise attempting to compensate. As another example, an irrigation probe may be used to maintain visibility during a surgical procedure and/or to maintain a desired pressure within a cavity, such as the posterior segment of the eye. The flow rate of an irrigation probe may be altered, which may cause an unwanted deviation from a safe intraocular pressure. When the power loss ends, the performance of the vitrectomy cutter or the irrigation probe may change again. The restored, normal performance may cause additional material to be removed that was not intended to be removed or may cause a sudden increase in intraocular pressure. The loss in power may also result in a computer reset as well, which can alter parameters and stop performance of some subsystems.

The present disclosure is more specifically directed to a system that monitors a voltage supplied by a main power supply to a power bus included in a system. When the voltage on the power bus drops below a threshold value, the power bus is connected to an alternate power supply that helps maintain the desired operating voltage. The desired voltage may be any voltage within a suitable operational range of the system or of a specific component or subsystem. When the main power supply is restored, the power bus is disconnected from the alternate power supply. The present disclosure includes circuits that provide for such monitoring and selective connecting and disconnecting in order to mitigate short-term power losses.

FIG. 1 illustrates an exemplary implementation of an ophthalmic surgical system, generally designated surgical system 100. While the present disclosure applies to many different types of surgical systems other than the exemplary ophthalmic surgical system 100 and to other medical systems, the surgical system 100 is described herein to provide appropriate context for the power loss mitigation systems, circuits, and methods described herein. As illustrated, the surgical system 100 includes a base housing or console 102 and an associated display screen 104 showing data relating to system operation and performance during an ophthalmic surgical procedure. In some implementations, the console 102 may be mobile. For example, some implementations may include wheels or casters 106 to facilitate movement as necessary or desirable. In some implementations, the console 102 may not include wheels. The console 102 may contain several subsystems that cooperate to enable a surgeon or other user to perform a variety of surgical procedures, such as ophthalmic surgical procedures.

An exemplary surgical instrument, which is illustrated as a probe 110, may be coupled to the console 102 by a conduit 108 and may form a part of the surgical system 100. The probe 110 represents any number of medical and/or surgical devices, including, for example, a vitrectomy probe, an illumination probe, an aspiration probe, an irrigation probe, a phacoemulsification device, a diathermy probe, or other types of medical devices. The probe 110 may be a handpiece, in some implementations. The probe 110 may be coupled to one or more subsystems included in the console 102. For example, the probe 110 may be coupled to a probe subsystem that facilitates control of a pump and/or a vacuum for use in the removal of vitreous or the irrigation of the posterior segment of an eye. The probe subsystem may also provide power to the probe 110 and control operation of the probe 110. The conduit 108 may include cables, tubes, wires, etc. to provide for the operation of the probe 110 in various implementations. As noted, in some implementations, the probe 110 may be an irrigation probe. In some implementations of the surgical system 100, the probe 110 may be coupled to multiple consoles, rather than to a single console 102 as illustrated. Such implementations may include other conduits in addition to the conduit 108 that connect the probe 110 to the consoles. The illustrated probe 110 may be used in various ophthalmic procedures, such as an anterior segment procedure, a posterior segment procedure, a vitreoretinal procedure, a vitrectomy procedure, a cataract procedure, and/or other procedures. Surgical procedures other than ophthalmic procedures may be performed by implementations of the system 100 and the probe 110.

Figure 2:
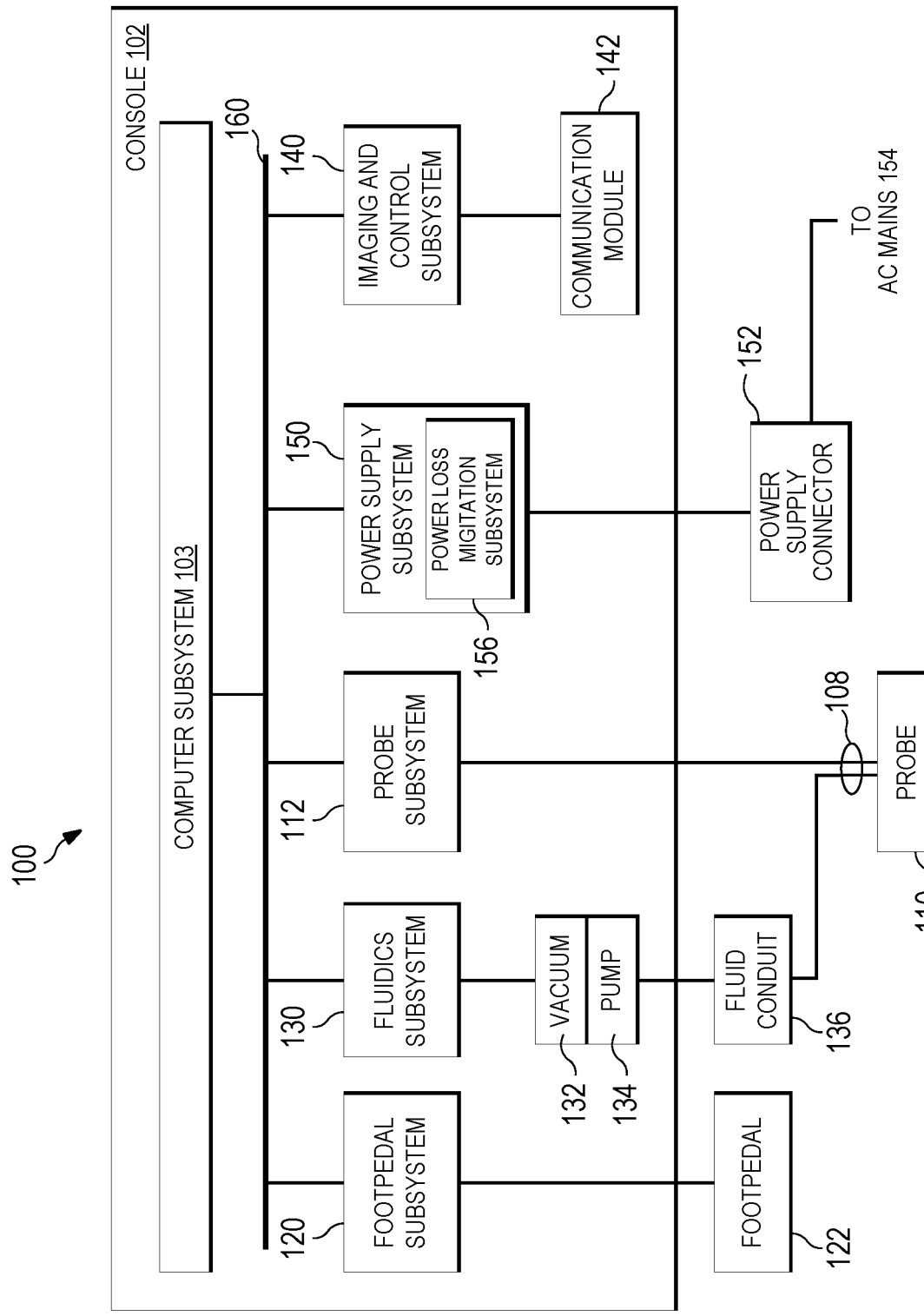
FIG. 2 is an illustration of an exemplary block diagram of the surgical system of FIG. 1.

FIG. 2 is a block diagram of an implementation of the surgical system 100 including the console 102 and further depicting several subsystems contained therein. The console 102 includes a computer subsystem 103 configured to communicate with the display screen 104 (FIG. 1), and includes a number of subsystems that are used together to perform surgical procedures, including ophthalmic surgical procedures, such as emulsification or vitrectomy surgical procedures, for example. The computer subsystem 103 may include one or more processing devices, such as a central processing unit or central processor, and an information or data storage system. The data storage system may include one or more types of memory, such as RAM, ROM, flash memory, a disk-based hard drive, and/or a solid-state hard drive. The processing devices and storage system may communicate over a bus 160, which may also permit communication with and between one or more of the subsystems of the surgical system 100.

Some examples of subsystems in the implementation shown in FIG. 2 may include a footpedal subsystem 120 including, for example, a footpedal 122, and a fluidics subsystem 130 including an aspiration vacuum 132 and an irrigation pump 134 that connect to a fluid conduit 136. The fluid conduit 136 or a portion thereof may extend between the console 102 and the probe 110 through the conduit 108 (FIG. 1). The surgical system 100 may further include a probe subsystem 112, including the probe 110, and an imaging and control subsystem 140 that is coupled to a communication module 144. The imaging and control subsystem 140 and the communication module 144 may facilitate control of the probe 110 and/or the subsystems and other features illustrated in FIG. 2.

The surgical system 100 includes a power supply subsystem 150 that receives electrical power from electrical AC mains 154 disposed within the surgical environment of the surgical system 100. For example, the power supply subsystem 150 may be coupled by the power supply connector 152 to an outlet or outlets disposed within an operating room in a hospital or surgical center. The power supply subsystem 150 may be coupled to a power bus to distribute power within the console 102 to the computer subsystem 103 and to the subsystems 112, 120, 130, 140, and to other subsystems included in other implementations of the surgical system 100. The bus 160 may include one or more power buses and one or more communication buses to provide power to and communication lines between the various components of the surgical system 100. The power supply subsystem 150 may also condition electrical power received from the AC mains 154. For example, the power supply subsystem 150 may convert received AC electricity to one or more desired DC voltages and/or other AC voltages. DC voltages, such as 12 V, 24 V, 48 V, may be distributed by multiple power buses, in some implementations. The other AC voltages may differ in amplitude and/or frequency. For example, the power supply subsystem 150 may convert 50 Hz AC voltage to 60 Hz AC voltage.

The power supply subsystem 150 may further include a power loss mitigation subsystem 156. The power loss mitigation subsystem 156 may monitor electricity provided by the power supply subsystem 150 to the various components of the surgical system 100. When the power loss mitigation subsystem 156 detects that a voltage has fallen below a threshold value, the power loss mitigation subsystem 156 may activate an alternate power supply. In some implementations, the power loss mitigation subsystem 156 may detect that a difference between the voltage and the threshold value has exceeded a threshold. The power loss mitigation subsystem 156 may monitor for the restoration of the power supply and disconnect the alternate power supply when the voltage rises back above the threshold value. In this way, the power loss mitigation subsystem 156 may compensate for power losses, i.e., voltage drops below a threshold value or a complete loss of power to maintain continuous power to the surgical system 100. The power losses may be short-term power losses such as power losses lasting a few hundred milliseconds, a second, or more. Some implementations of the power loss mitigation subsystem 156 may maintain power supplies for at least 500 ms, enabling at least some components of the surgical system 100 to operate unaffected by the power loss.

Figure 3:
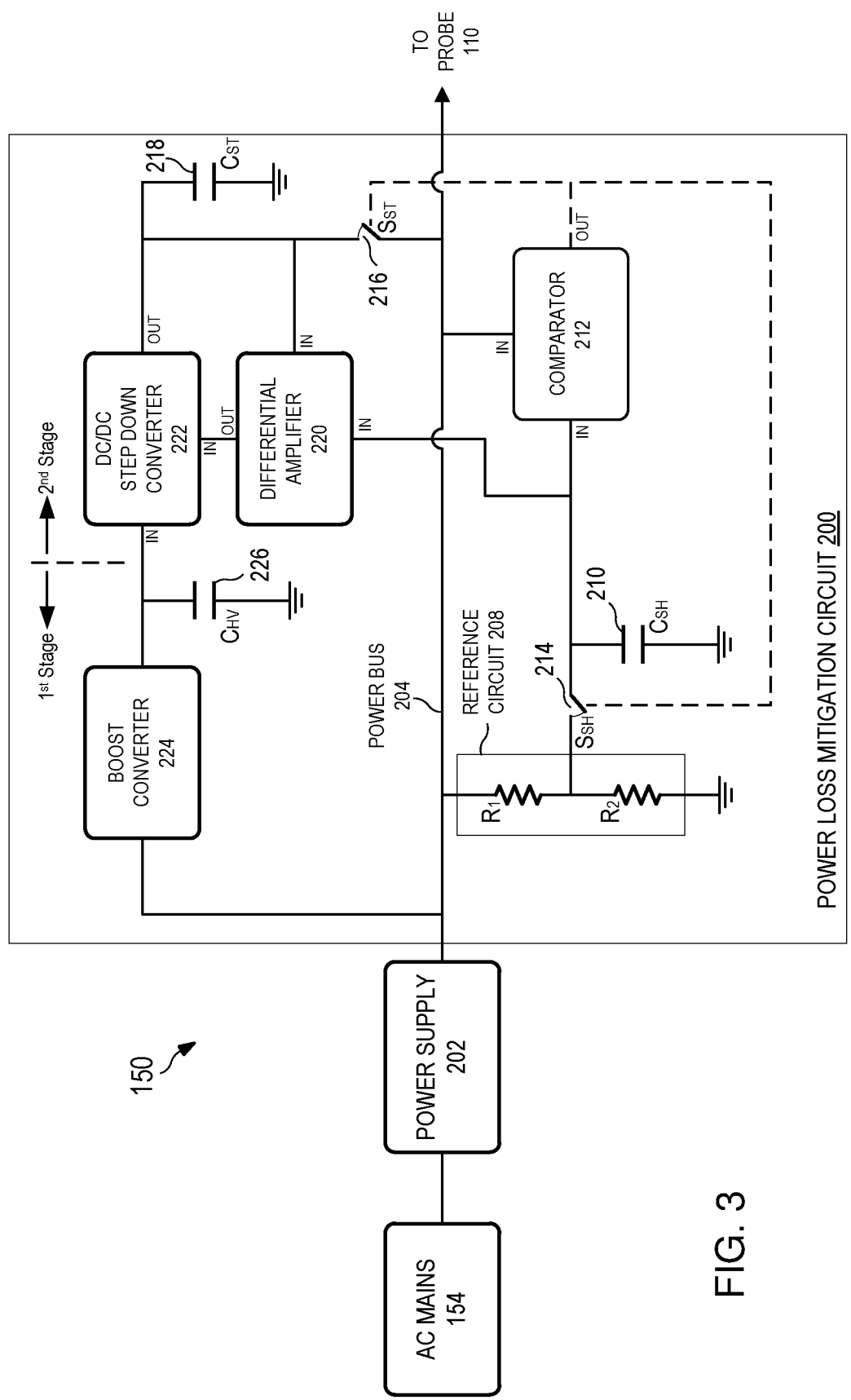
FIG. 3 is a circuit diagram illustrating an exemplary circuit-based implementation of a power loss mitigation system.

Referring now to FIG. 3, shown therein is a power loss mitigation circuit 200, which may be an implementation of the power loss mitigation subsystem 156 of the power supply subsystem 150. The power supply subsystem 150 may include a power supply 202. The power supply 202 may receive AC electricity from the AC mains 154 and convert the AC electricity to DC to be distributed to the components of the surgical system 100. As an example, the power supply 202 may be a 24 VDC power supply providing 24 V on a power bus 204. The power bus 204 may connect to any of the subsystems of the surgical system 100, including those illustrated in FIG. 2 and/or any of the devices connected to the console 102, including the probe 110. The power bus 204 may be, or be a component of, the bus 160 of FIG. 2. As illustrated, the power bus 204 is coupled to the probe 110 to provide power to components thereof, such as an oscillating vitreous cutter or to controls and circuits contained on or within an irrigation probe. As another example, the power bus 204 may be coupled to the fluidics subsystem 130 including the vacuum 132 and the pump 134 (FIG. 2).

FIG. 3 also illustrates details of the power loss mitigation circuit 200. The power loss mitigation circuit 200 includes various components configured so as to detect undesired, excessive drops in power and to engage an alternate power supply for a period of time to prevent adverse consequences that may result from a complete loss of power or from a power loss that goes beyond normal operating conditions.

To monitor the power provided by the power bus 204, the loss mitigation circuit 200 may include a reference circuit 208 that provides a reference value for comparison with the power supply voltage. When the voltage on the power bus 204 drops below the threshold value provided by the reference circuit 208, the circuit 200 may operate to connect to the power bus 204 to an alternate power supply, as will be described in further detail. As illustrated in FIG. 3, the reference circuit 208 comprises a pair of resistors $R_1$ and $R_2$ configured as a voltage divider. In other implementations, the reference circuit 208 may be provided by a low-pass RC filter or a capacitive divider. The reference circuit 208 may be configured to provide any desired threshold voltage value as a fraction or proportion of a normal operating voltage. The desired threshold voltage value may be within a normal operating range. As illustrated, the values of the resistors $R_1$ and $R_2$ determine the threshold value as compared with the voltage on the power bus 204. As illustrated, $R_1$ and $R_2$ may be selected to provide a threshold value of 95% of the normal operating voltage on the power bus 204. For example, when the power supply 202 provides 24 V to the power bus 204, the reference circuit 208 may provide the threshold value or reference voltage of 22.8 V. To provide the 95% threshold value, $R_1$ may be a 5 kOhm resistor and $R_2$ may be a 95 kOhm resistor, for example. Other threshold values and resistor values may be used in other implementations. The threshold value may be equal to or close in value to a low end of a normal operating voltage range of devices or subsystems coupled to the power bus 204. In some implementations, the threshold value may be determined specifically by the voltage requirements of a device used to directly interact with the patient during a surgical procedure. For example, the voltage requirements of the probe 110 may be used to determine the threshold value without regard to the voltage requirements of the footpedal subsystem 120.

The reference circuit 208 provides the reference voltage to a sample and hold capacitor 210, $C_{SH}$, which is also coupled to an input of a comparator circuit or comparator 212. The voltage on the sample and hold capacitor 210 generally tracks the voltage on the power bus 204, when changes in the voltage on the power bus 204 are gradual. When the voltage on the power bus 204 changes quickly, such as from a sudden power loss, the voltage on the capacitor 210 may not respond immediately, such that the voltage on the power bus 204 and the voltage on the capacitor 210 depart from their normal proportional relationship. Some implementations of the sample and hold capacitor 210 may have a capacitance ranging from about 0.5 µF to about 1 µF. Other ranges may be used in other implementations. The comparator 212 may be an operational amplifier based comparator or another comparator circuit. An additional input of the comparator 212 may be coupled to the power bus 204. The comparator 212 may receive a voltage from the power bus 204 and the reference voltage from the reference circuit 208 (when the switch 214 is closed and from the capacitor 210 when the switch 214 is open) and may compare them to each other in order to provide a self-adjusting control signal that causes switches in the power loss mitigation circuit 200 to open or close, when the reference voltage and voltage on the power bus 204 diverge. The switch 214 may be referred to herein as the sample and hold switch or $S_{SH}$.

Under normal conditions, the switch 214 may be closed to facilitate comparison of the voltage on the power bus 204 with the reference voltage and allow the capacitor 210 to track the voltage on the power bus during normal operation. Allowing the capacitor 210 to track the voltage on the power bus 204 allows the power loss mitigation circuit 200 to adjust to normal fluctuations caused by changes in temperature, operational drift, etc. The output of the comparator 212 may be coupled to the switch 214 and to a switch 216, which may be referred to as a standby power switch 216 or SST. The switch 216 may be open under normal power conditions. When the voltage on the power bus 204 suddenly drops below the reference voltage provided by the reference circuit 208, the output of the comparator 212 causes the switch 214 to open and the switch 216 to close. Opening the switch 214 disconnects the capacitor 210 from the power bus 204, preventing the voltage on the capacitor 210 from dropping along with the voltage on the power bus 204. Closing the switch 216 couples the power bus 204 to a capacitor 218. The capacitor 218 is also referred to as a standby capacitor 218 or $C_{ST}$. The capacitor 218 is precharged to the voltage level across the capacitor 210. Some implementations of the standby capacitor 218 may have a capacitance ranging from 200 µF to about 500 µF. Other implementations of the standby capacitor 218 may have a lower or a higher capacitance. When connected to the power bus, the standby capacitor 218 may provide power to the power bus 204 such that the power bus 204 maintains a voltage approximately equal to the desired reference voltage, e.g., 95% of the normal operating voltage on the power bus 204.

After the power loss ends and the voltage on the power bus 204 is returned to 24 V by the power supply 202 (referred to in this example as "normal conditions"), the signal at the output of the comparator 212 opens the standby switch 216 and closes the sample and hold switch 214. In this way, the power loss mitigation circuit 200 responds to the restoration of power. Opening the standby switch 216 disconnects the power bus 204 from the standby capacitor 218 and closing the sample and hold switch 214 reconnects the reference circuit 208 to the sample and hold capacitor 210 and to the input of the comparator 212, reconnecting the sample and hold capacitor 210 to the power bus 204.

The sample and hold capacitor 210 may also be coupled to an input of a differential amplifier 220. The differential amplifier 220 may include an additional input coupled to the standby capacitor 218. The signals (voltages) received at the inputs of the differential amplifier 220 may be processed by the differential amplifier 220 to generate an output signal. The output of the differential amplifier 220 may be coupled to a DC/DC step down converter 222. The differential amplifier 220, which may be implemented by an operational amplifier in some instances, interacts with the DC/DC step down converter 222 to ensure that the voltage on the standby capacitor 218 tracks the voltage on the sample and hold capacitor 210. The differential amplifier 220 provides a feedback signal to the DC/DC step down converter 222. For example, when the reference circuit 208 provides a reference voltage that is 95% of the normal voltage on the power bus 204, the sample and hold capacitor is charged to 22.8 V (when the normal voltage is 24 V). The 22.8 V is provided as an input to the differential amplifier 220. The differential amplifier 220 outputs a signal to the DC/DC step down converter 222 to ensure that the output of the converter 222 is also 22.8 V, causing the other input of the converter 222 to match the input from the sample and hold capacitor 218.

In order to supply power to the DC/DC step down converter 222, a boost converter 224 is connected between the DC/DC step down converter 222 and the power bus 204, as a first stage of an alternate power supply. The boost converter 224 may receive power from the power bus 204 and generate a high voltage output which is coupled to an input of the DC/DC step down converter 222. The boost converter 224 may double the voltage received at the input, in some implementations. For example, when the power bus 204 is at 24 V, the boost converter 224 may charge a high-voltage capacitor 226 or $C_{SH}$ to 48 V. In some implementations, the boost converter 224 may increase the received voltage by more than a factor of two. Accordingly, the high-voltage capacitor 226, coupled to the boost converter 224, may be rated to 60 V or more, such as several hundred volts, in some implementations. Implementations of the capacitor 226 may have a capacitance ranging from 2 µF to about 1000 µF. The greater the capacitance of the high-voltage capacitor 226, the greater the amount of time during which a power loss can be mitigated. When power is to be provided by the standby capacitor 218, acting as an alternate power supply, the standby capacitor 218 may be powered by the high-voltage capacitor 226 via the DC/DC step down converter 222.

In this way, the alternate power supply may be implemented as a two-stage power source, in which the boost converter 224 and the high-voltage capacitor 226 provide the first stage and the DC/DC step down converter 222 and the standby capacitor 218 provide the second stage. By having the alternate power supply provided by a two-stage power source, the first stage may permit a higher voltage than is desired at the output of the alternate power supply. The energy stored on the high-voltage capacitor 226 is proportional to the square of the voltage, such that the higher voltage on the first stage provides more energy storage. The second stage may provide the energy, stored in the first stage, at the desired voltage at the output of the alternate power supply.

The use of the standby capacitor 218 and the high-voltage capacitor 226 to mitigate short-term power losses may provide advantages over battery-based loss mitigation systems. For example, the capacitors 218 and 226 are essentially maintenance free, unlike battery-based power backup alternatives. In some implementations, the power loss mitigation circuit 200 may be configured to provide power to only a subset of the subsystems and instruments connected to the console 102 of FIG. 1. In such implementations, additional alternate power supply systems may be included in the console 102. For example, a battery-based backup power supply may be able to supply power to the computing system 103 during a power loss, while the power loss mitigation circuit 200 may supply continuous power to the probe 110. In some implementations, more than one power loss mitigation circuit 200 may be included in the console 102.

Figure 4:
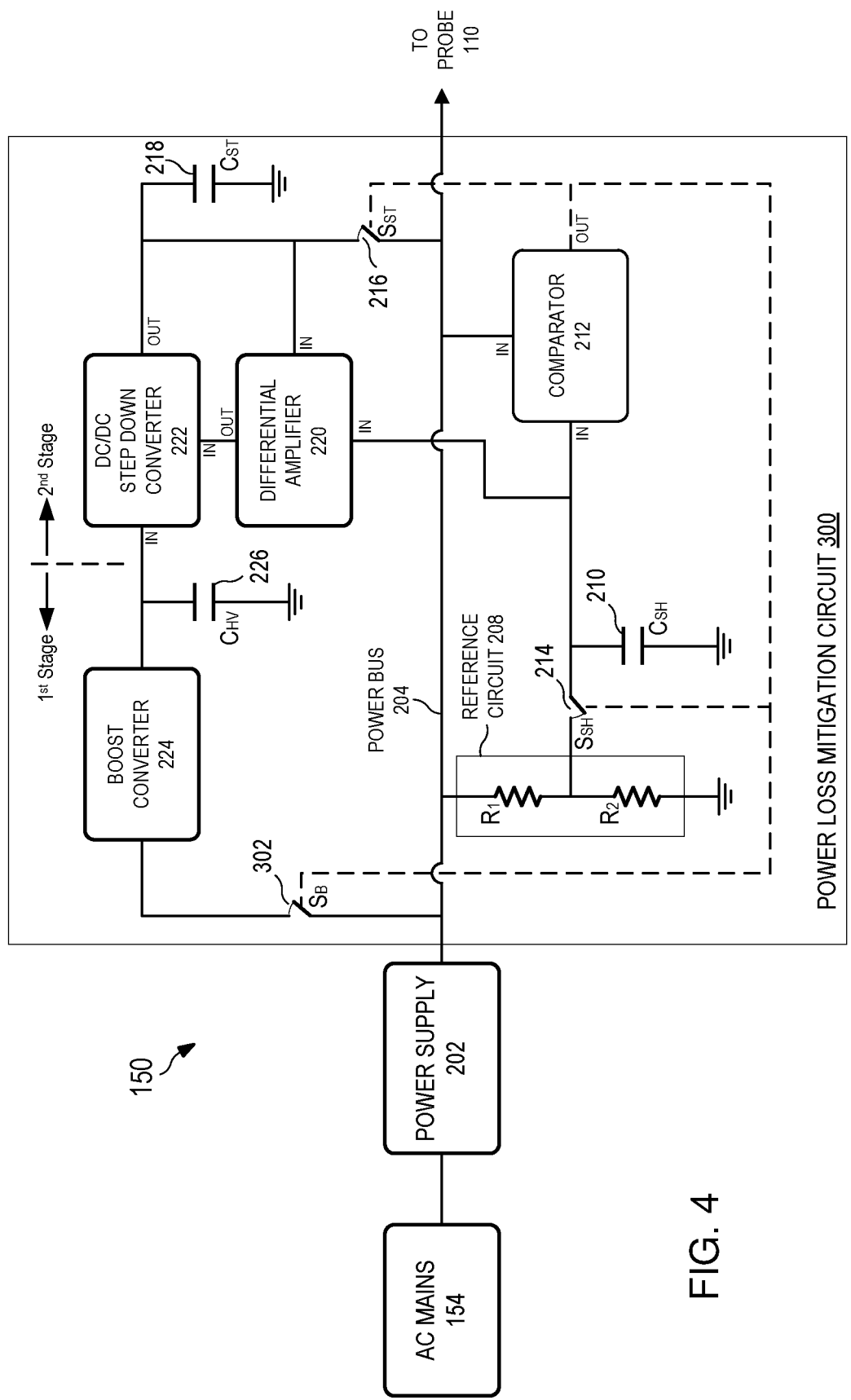
FIG. 4 is a circuit diagram illustrating another exemplary circuit-based implementation of a power loss mitigation system.

Referring now to FIG. 4, shown therein is a power loss mitigation circuit 300 that is similar in many respects to the power loss mitigation circuit 200 of FIG. 3. The power loss mitigation circuit 300 may be included in the power supply subsystem 150 as the power loss mitigation subsystem 156 of FIG. 2. In addition to the features described with respect to the power loss mitigation circuit 200, the power loss mitigation circuit 300 may further include a boost switch 302 (labeled as SB). The boost switch 302 may be coupled to the output of the comparator 212, like the standby switch 216 and the sample and hold switch 214. Under normal operating conditions, e.g., in the absence of a power loss or a power loss that is less than a threshold amount, the boost switch 302 may be in a closed position to couple the boost converter 224 to the power bus 204. This may allow the high-voltage capacitor 226 to be charged as an alternative power supply in the event of a power loss. When the voltage on the power bus 204 drops below the threshold value, the output signal from the comparator 212 may cause the standby switch 216 to close, the sample and hold switch 214 to open, and the boost switch 302 to open. Opening the boost switch 302 disconnects the boost converter 224 from the power bus 204, which may prevent the boost converter 224 from continuing to draw from the power bus 204.

Figure 5:
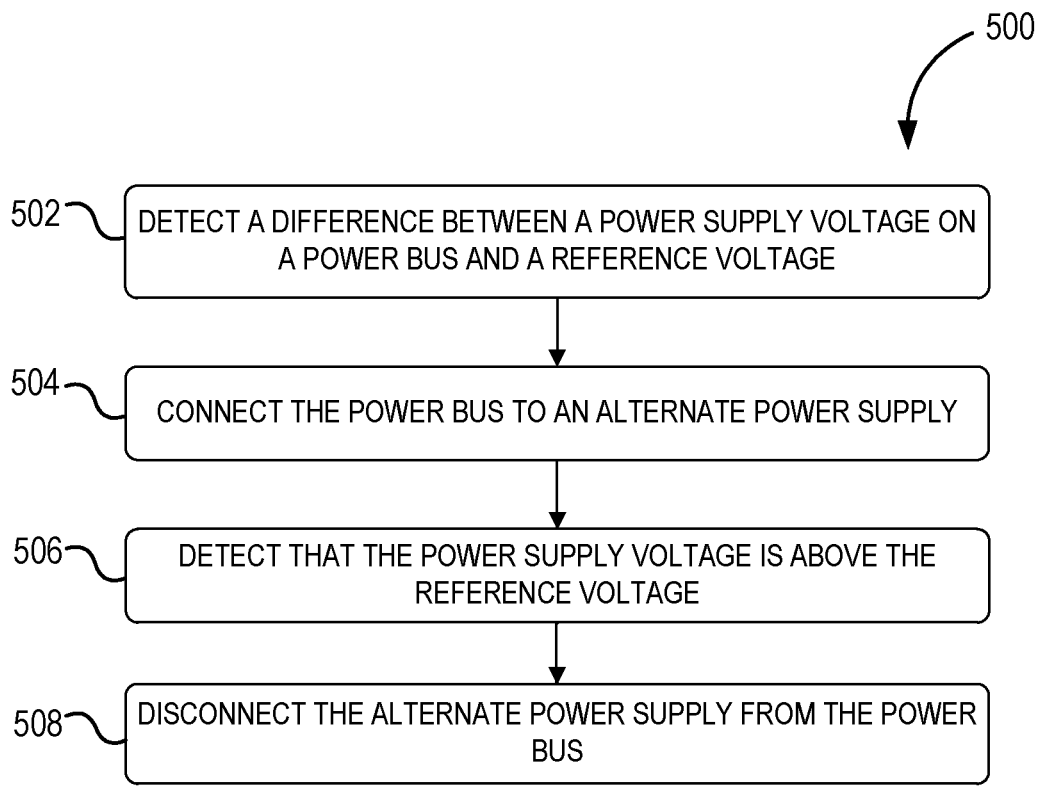
FIG. 5 is a flowchart of an exemplary method of mitigating a short-term power loss in a surgical system, such as the surgical system of FIG. 1.

Referring now to FIG. 5, shown therein is flowchart of an exemplary method 500 of a mitigating short-term power loss in a medical system. As illustrated, the method 500 includes several enumerated steps or operations. Additional operations may be included before, after, in between, or as part of the enumerated operations. The method 500 may be implemented by a system or a circuit. For example, the method 500 may be implemented by the power supply subsystem 150 of the surgical system 100 (FIG. 2) or by the power loss mitigation circuits 200 or 300 of FIGS. 3 and 4, respectively.

At 502, a comparator may detect a difference between a power supply voltage on a power bus and a reference voltage. With respect to the power loss mitigation circuit 200, this may be performed by the comparator 212, which is configured to receive the power supply voltage from the power bus 204 and the reference voltage from the reference circuit 208, when the sample and hold switch 214 is closed, and from the sample and hold capacitor 210, when the switch 214 is open. The comparator may detect that the voltage on the power bus is less than the reference voltage.

At 504, the power bus may be connected to an alternate power supply. For example, the comparator 212 may detect that the power supply voltage on the power bus 204 is below the reference voltage and generate an output control signal that causes the sample and hold switch 214 to open and the standby switch 216 to close. When the standby switch 216 closes, the power bus 204 may be connected to the first and second stages of an alternate power supply. The first stage of the alternate power supply may include the boost converter 224 and the high-voltage capacitor 226, while the second stage of the alternate power supply may include the DC/DC step down converter 222 and the standby capacitor 218. An output of the differential amplifier 220 may be coupled to the DC/DC step down converter 222 to control the converter 222 to provide charge to the standby capacitor 218 from the high-voltage capacitor 226.

At 506, the power supply voltage on the power bus may be detected to be above the reference voltage. For example, after a period time of, such as 300 ms or 700 ms, the power loss may be resolved and the power supply 202 may resume supplying a desired voltage on the power bus 204. The power supply voltage may be detected by the comparator 212 as being greater than the voltage across the sample and hold capacitor 210. The comparator 212 may generate control signals, which may be digital control signals or analog control signals, to cause the standby switch 216 to open and the sample and hold switch 214 to close, thereby disconnecting the alternate power supply from the power bus 204, at 508.

In some implementations of the method 500, the boost switch 302 of FIG. 4 may be disconnected or switched off at 504, after the power supply voltage on the power bus 204 is determined to be less than the reference voltage, e.g. outside the normal operating range. The boost switch 302 may be reconnected or switched on as part of 508 after the power supply voltage is detected as being above the reference voltage. In some implementations, the power bus 204 may be connected to the standby capacitor 218 for less than 2 seconds. In some implementations, the capacitors 226 and 218 may be able to provide power for at least 500 ms.

In some implementations, the method 500 may include an operation of measuring a duration of a power loss. For example, the computer subsystem 103 may monitor the power loss mitigation subsystem 156 of FIG. 1 to measure how long the switch 214 is open or how long the switch 216 is closed. For example, the power loss mitigation subsystem 156 may be configured to provide for a continuous power supply on the power bus 204 for more than a second. At an intermediate point in time (e.g., at 500 ms), the computer subsystem 103 may take certain mitigating actions. For example, the computer subsystem 103 may generate commands to save data, alert a user, and/or put one or more of the subsystems into safe mode, in anticipation of a power loss of a longer duration than can be sustained by the power loss mitigation subsystem 156. In this way, even when the power loss exceeds the ability of the power loss mitigation subsystem 156 to provide power, implementations of the power loss mitigation subsystem 156 may provide time to take actions to mitigate such longer power loss.

Implementations of the present disclosure may include surgical systems, circuits, and methods for providing a short-term alternate power supply when a main power supply experiences a power loss. The alternate power supply may include one or more capacitors that may be charged during normal operation of the surgical system. The alternate power supply may be included within the surgical system alongside one or more additional alternate power supplies. The alternate power supply may be configured to supply power to a surgical instrument to minimize potential risks that could be caused to a patient as a result of a power loss. The alternate power supply may provide a maintenance-free power source during power losses lasting for more than 500 ms or more than one second. The alternate power supply may be automatically engaged when the voltage on a power bus drops below a minimum threshold and automatically disengaged when the voltage on the power bus rises above the minimum threshold again. In this manner, embodiments of the present disclosure may provide a self-adjusting short-term alternate power supply to minimize potential risks to a patient during a surgical procedure.

Persons of ordinary skill in the art will appreciate that the implementations encompassed by the present disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A surgical system comprising:
a surgical instrument subsystem that couples to a surgical instrument; and
a power supply subsystem coupled to the surgical instrument subsystem, the power supply subsystem comprising:
a main power supply connectable to AC mains to generate a voltage;
a power bus connected to the main power supply;
an alternate power supply comprising at least two capacitors, wherein the at least two capacitors comprise a first capacitor for tracking a voltage on the power bus and a second capacitor to provide standby voltage to the power bus when connected to the power bus; and a circuit that monitors the voltage on the power bus for powering the surgical instrument subsystem and automatically connects the power bus to the second capacitor of the alternate power supply when the voltage drops below a reference voltage due to a power loss from the main power supply;

wherein the second capacitor provides the stand-by voltage to the power bus when connected to the power bus such that the power bus can maintain the voltage while the second capacitor is charged;

wherein the circuit automatically connects the power bus back to receiving power from the main power supply when the power loss is discontinued; and wherein the second capacitor is recharged while the power bus is receiving power from the main power supply.

2. The surgical system of claim 1, further comprising:
a computing system configured to operate the surgical system based on inputs from a user;
wherein the computing system is configured to measure a duration of power loss and take mitigating actions in anticipation of the power loss lasting longer than power can be sustained to the surgical instrument subsystem by the power supply subsystem.

3. The surgical system of claim 1, wherein the alternate power supply comprises a two-stage alternate power supply.

4. The surgical system of claim 3, wherein a first stage of the two-stage alternate power supply is coupled to the power bus and the first capacitor and wherein a second stage of the two-stage alternate power supply is coupled to the second capacitor that is coupled to the power bus by a switch.

5. The surgical system of claim 1, wherein the reference voltage is provided by a reference circuit having an output connected to the circuit by a switch.

6. The surgical system of claim 4, wherein the first stage of the two-stage alternate power supply comprises a boost converter and the first capacitor configured to store electrical energy.

7. The surgical system of claim 6, wherein the boost converter is coupled to the power bus by a switch that is opened when the power bus is connected to the alternate power supply.

8. The surgical system of claim 1, wherein the power supply subsystem further comprises a differential amplifier that receives the reference voltage and an output voltage of the alternate power supply as inputs and generates a control signal for a step down converter included in the power supply subsystem.

9. The surgical system of claim 1, wherein the at least one surgical instrument subsystem comprises an irrigation probe, and wherein the irrigation probe is coupled to a console by a, conduit, the console containing the alternate power supply.

10. The surgical system of claim 1, wherein the alternate power supply is coupled to the power bus at an input and includes the first capacitor coupled by a step down converter to the second capacitor at an output.

11. The surgical system of claim 1, wherein the alternate power supply comprises a two-stage alternate power supply, wherein a first stage of the two-stage alternate power supply is coupled to the power bus at an input and to the first capacitor at an output and wherein a second stage of the two-stage alternate power supply is coupled to the first capacitor at an input and to the second capacitor at an output, and wherein the second stage of the two-stage alternate power supply is coupled to the power bus by a switch.

12. The surgical system of claim 1, wherein the circuit is a comparator having an output coupled to a switch.

13. The surgical system of claim 12, wherein comparator has the output coupled to the switch at an input to a first stage of the alternate power supply and a switch at an output of a second stage of the alternate power supply.

14. The surgical system of claim 1, wherein the reference voltage is provided by a reference circuit having an output connected to the circuit by a switch that is automatically opened when the voltage drops below reference voltage due to the power loss from the main power supply.

15. The surgical system of claim 7, further comprising a third capacitor, wherein the boost converter charges the third capacitor when the power bus is receiving power from the main power supply.

16. The surgical system of claim 15, further comprising a step down converter, wherein the second capacitor receives charge from the third capacitor via the step down converter when the second capacitor is providing power to the power bus.

* * * * *